US007972702B2

(12) United States Patent
Tanabe

(10) Patent No.: US 7,972,702 B2
(45) Date of Patent: Jul. 5, 2011

(54) DEFECT INSPECTION METHOD FOR A GLASS SUBSTRATE FOR A MASK BLANK, GLASS SUBSTRATE FOR A MASK BLANK, MASK BLANK, EXPOSURE MASK, METHOD OF PRODUCING A GLASS SUBSTRATE FOR A MASK BLANK, METHOD OF PRODUCING A MASK BLANK, AND METHOD OF PRODUCING AN EXPOSURE MASK

(75) Inventor: Masaru Tanabe, Tokyo (JP)

(73) Assignee: Hoya Corporation, Tokyo (JP)

( * ) Notice: Subject to any disclaimer, the term of this patent is extended or adjusted under 35 U.S.C. 154(b) by 660 days.

(21) Appl. No.: 11/450,394

(22) Filed: Jun. 12, 2006

(65) Prior Publication Data

US 2007/0003843 A1    Jan. 4, 2007

(30) Foreign Application Priority Data

Jun. 10, 2005 (JP) ................. 2005-171153

(51) Int. Cl.
  *B32B 17/06* (2006.01)
(52) U.S. Cl. .......................... 428/426; 428/98
(58) Field of Classification Search ............. 250/559.45;
     438/106, 121; 428/426, 98
  See application file for complete search history.

(56) References Cited

U.S. PATENT DOCUMENTS

| 6,610,994 | B1 | 8/2003 | Tanabe |
| 2001/0044052 | A1* | 11/2001 | Tanabe ............... 430/5 |
| 2003/0218145 | A1* | 11/2003 | Tanabe .......... 250/559.45 |

FOREIGN PATENT DOCUMENTS

| JP | 62213262 A | 9/1987 |
| JP | 1189654 A | 7/1989 |
| JP | 8-031723 A | 2/1996 |
| JP | 8-261953 A | 10/1996 |
| JP | 11242001 A | 9/1999 |
| JP | 2002131884 A | 5/2002 |
| JP | 2003-081654 A | 3/2003 |
| JP | 2006220905 A | 8/2006 |
| JP | 2007086050 A | 4/2007 |

OTHER PUBLICATIONS

Japanese Office Action corresponding to Japanese Patent Application No. 2005-171153, dated Oct. 18, 2010, Partial English language translation.

* cited by examiner

*Primary Examiner* — Timothy M Speer
*Assistant Examiner* — Lauren Robinson
(74) *Attorney, Agent, or Firm* — Sughrue Mion, PLLC

(57) ABSTRACT

On inspecting a glass substrate for a mask blank which substrate has surfaces including one end face, the glass substrate is prepared to have the one end face which has a chamfered surface and a remaining surface serving as a side surface. The chamfered surface of the one end face is smaller in width than a chamfered surface of an opposite end face of the glass substrate. A short-wavelength light having a wavelength of 200 nm or less is introduced into the side surface of the one end face. From either the one end face or a different surface of the surfaces of the glass substrate, a long-wavelength light is received which is longer in wavelength than the short-wavelength light and which is generated by an internal defect of the glass substrate in response to the short-wavelength light. The internal defect is detected with reference to the long-wavelength light.

8 Claims, 7 Drawing Sheets

DEFECT INSPECTION METHOD FOR A GLASS SUBSTRATE FOR A MASK BLANK, GLASS SUBSTRATE FOR A MASK BLANK, MASK BLANK, EXPOSURE MASK, METHOD OF PRODUCING A GLASS SUBSTRATE FOR A MASK BLANK, METHOD OF PRODUCING A MASK BLANK, AND METHOD OF PRODUCING AN EXPOSURE MASK

This application claims priority to prior Japanese patent application JP 2005-171153, the disclosure of which is incorporated herein by reference.

BACKGROUND OF THE INVENTION

This invention relates to a defect inspection method of inspecting internal defects of a glass substrate for a mask blank, a glass substrate for a mask blank to be inspected by the defect inspection method, a mask blank produced from the glass substrate, an exposure mask produced from the mask blank, a method of producing a glass substrate for a mask blank after inspecting internal defects of the glass substrate, a method of producing a mask blank by the use of the glass substrate, and a method of producing an exposure mask by the use of the mask blank.

In recent years, following a miniaturization of a semiconductor device, an exposure light having a shorter wavelength is used in the photolithography. For example, an ArF excimer laser (having an exposure wavelength of 193 nm) and a F2 excimer laser (having an exposure wavelength of 157 nm) are used as the exposure light. In an exposure mask used in the photolithography and a mask blank used to produce the exposure mask, development is rapidly carried out of a light shielding film (opaque film) having a light shielding function for the exposure wavelength of the exposure light and a phase shift film having a phase shifting function and various film materials are proposed.

It is required that the above-mentioned glass substrate for a mask blank and a synthetic silica glass substrate used for producing the glass substrate for a mask blank do not have a defect, such as a foreign matter or an air bubble, present inside. Japanese Unexamined Patent Application Publication (JP-A) No. H8-261953 discloses a defect inspection apparatus for detecting internal defects (such as foreign matters or air bubbles) present in a glass substrate by introducing a He—Ne laser beam into the glass substrate and detecting a scattered light scattered by the internal defects.

However, even if the exposure mask is produced by the use of the synthetic silica glass substrate and the glass substrate for a mask blank which are judged by the above-mentioned defect inspection apparatus to have no internal defect, a transfer pattern defect derived from the glass substrate (which will later be described) may be caused during pattern transfer in which a mask pattern of the exposure mask is transferred to a semiconductor substrate by the use of an ArF excimer laser as the exposure light.

This is presumably because some internal defects (such as local cords (local striae), inclusions, heterogeneous matters) present in the glass substrate locally change optical characteristics (for example, decrease transmittance) when a high-energy light such as an ArF excimer laser beam or a F2 excimer laser beam is used as the exposure light although no scattering occurs when a visible light laser beam such as a He—Ne laser beam is used as the exposure light.

SUMMARY OF THE INVENTION

It is therefore an object of this invention to provide a defect inspection method for a glass substrate for a mask blank, which is capable of successfully detecting internal defects in a substantially entire region of the glass substrate, including those internal defects in the vicinity of a principal surface thereof.

It is another object of this invention to provide a glass substrate for a mask blank, a mask blank, and an exposure mask, which are produced by the use of the above-mentioned defect inspection method.

It is still another object of this invention to provide a method of producing an exposure mask, which is capable of improving a transfer accuracy of pattern transfer by successfully detecting internal defects in a substantially entire region of a glass substrate for a mask blank, including those internal defects in the vicinity of a principal surface thereof which have a great influence when pattern transfer to an object is carried out.

It is yet another object of this invention to provide a method of producing a mask blank for use in producing the above-mentioned exposure mask, a method of producing a glass substrate for use in producing the above-mentioned mask blank.

According to an aspect of the invention, the short-wavelength light having a wavelength of 200 nm or less is introduced into the glass substrate for a mask blank and used in inspection of internal defects of the glass substrate. Therefore, it is possible to successfully detect internal defects which become transfer pattern defects upon pattern transfer using an exposure mask produced from the glass substrate and an exposure light.

Further, the chamfered surface of the one end face of the glass substrate for a mask blank has a width smaller than that of the chamfered surface of the opposite end face opposite to the one end face. Therefore, in a surface layer region of the glass substrate from the principal surface adjacent to the small-width chamfered surface to the depth corresponding to the width of the small-width chamfered surface, the short-wavelength light introduced perpendicularly to a side surface of the one end face is refracted at the small-width chamfered surface and propagates through the glass substrate without reaching the opposite end face so that the internal defects present in the surface layer region can not be detected. On the other hand, in a remaining region of the glass substrate except the surface layer region, the short-wavelength light introduced to the one end face reaches the opposite end face so that the internal defects in the remaining region can be detected. It is noted that the surface layer region is eventually removed in a polishing step to be carried out later and, therefore, no problem occurs even if the internal defects are present in the surface layer region. Thus, it is possible to successfully detect the internal defects in a substantially entire region of the glass substrate, including those internal defects in the vicinity of the principal surface on which a mask pattern is to be formed when an exposure mask is produced from the glass substrate (i.e., those internal defects having a great influence when pattern transfer to an object is performed by the use of the exposure mask).

According to an aspect of the invention, if the chamfered surface formed on the one end face of the glass substrate and having a width smaller than that of the chamfered surface of the opposite end face may be formed on each of opposite sides of the one end face adjacent to opposite principal surfaces of the glass substrate, respectively. In this case, in a region of the glass substrate from the depth corresponding to the width of the chamfered surface of the one end face to the depth corresponding to the width of the chamfered surface of the opposite end face, the light introduced into the one end face and a light thus introduced and then totally reflected by the chamfered surface of the opposite end face propagate. Therefore, it is possible to improve a sensitivity of detection of the internal defects in the above-mentioned region.

According to an aspect of the invention, the width of the chamfered surface of the one end face through which the inspection light for use in detecting the internal defects (for example, the short-wavelength light having a wavelength of 200 nm or less) is introduced is smaller than that of the chamfered surface of the opposite end face opposite to the one end face. Therefore, in a surface layer region of the glass substrate from the principal surface adjacent to the small-width chamfered surface to the depth corresponding to the width of the small-width chamfered surface, the inspection light introduced perpendicularly to a side surface of the one end face is refracted at the small-width chamfered surface and propagates through the glass substrate without reaching the opposite end face so that the internal defects present in the surface layer region can not be detected. On the other hand, in a remaining region of the glass substrate except the surface layer region, the inspection light introduced to the one end face reaches the opposite end face so that the internal defects in the remaining region can be detected. It is noted that the surface layer region is eventually removed in a polishing step to be carried out later and, therefore, no problem occurs even if the internal defects are present in the surface layer region. Thus, it is possible to successfully detect the internal defects in a substantially entire region of the glass substrate, including those internal defects in the vicinity of the principal surface on which a mask pattern is to be formed when an exposure mask is produced from the glass substrate (i.e., those internal defects having a great influence when pattern transfer to an object is performed by the use of the exposure mask).

According to an aspect of the invention, if the chamfered surface formed on the one end face and having a width smaller than that of the chamfered surface of the opposite end face may be formed on each of opposite sides of the one end face adjacent to opposite principal surfaces of the glass substrate, respectively. In this case, in a region from the depth corresponding to the width of the chamfered surface of the one end face to the depth corresponding to the width of the chamfered surface of the opposite end face, the light introduced from the one end face and a light thus introduced and then totally reflected by the chamfered surface of the opposite end face propagate. Therefore, it is possible to improve a sensitivity of detection of the internal defects in the above-mentioned region.

According to an aspect of the invention, at the stage of a mask blank or an exposure mask, the short-wavelength light having a wavelength of 200 nm or less is introduced to its end face to detect the internal defects. Thus, like in case of claim 3, 4, or 5, it is possible to successfully detect the internal defects in a substantially entire region of the glass substrate and to improve a sensitivity of detection.

According to an aspect of the invention, the short-wavelength light having a wavelength of 200 nm or less is introduced to the synthetic quarts glass substrate and used for inspection of internal defects of the glass substrate. Therefore, it is possible to successfully detect internal defects which become transfer pattern defects upon pattern transfer using the exposure light and an exposure mask which is produced from the synthetic silica glass substrate through the glass substrate for a mask blank and the mask blank. By producing the glass substrate for a mask blank by the use of the synthetic silica glass substrate for which no internal defect is detected, the exposure mask using the glass substrate for a mask blank does not have a region where optical characteristics locally changes (for example, transmittance is decreased) due to the internal defects of the glass substrate. Thus, it is possible to improve a transfer accuracy without causing the transfer pattern defects.

In the preparation step, the synthetic silica glass substrate is prepared in which the width of the chamfered surface of the one end face is smaller than that of the chamfered surface of the opposite end face opposite to the one end face. Therefore, in a surface layer region of the glass substrate from the principal surface adjacent to the small-width chamfered surface to the depth corresponding to the width of the small-width chamfered surface, the short-wavelength light introduced to the side surface of the one end face is refracted at the chamfered surface and propagates through the synthetic silica glass substrate to leak out without reaching the opposite end face so that the internal defects present in the surface layer region can not be detected. On the other hand, in a remaining region of the glass substrate except the surface layer region, the short-wavelength light introduced to the one end face reaches the opposite end face so that the internal defects in the remaining region can be detected. It is noted that the surface layer region is eventually removed in a polishing step to be carried out later and, therefore, no problem occurs even if the internal defects are present in the surface layer region. Thus, it is possible to successfully detect the internal defects in a substantially entire region of the glass substrate, including those internal defects in the vicinity of the principal surface on which a mask pattern is to be formed when an exposure mask is produced from the synthetic silica glass substrate (i.e., those internal defects having a great influence when pattern transfer to an object is performed by the use of the exposure mask). Therefore, by producing the exposure mask from the synthetic silica glass substrate for which no internal defect is detected, it is possible to improve a transfer accuracy upon pattern transfer using the exposure mask.

According to an aspect of the invention, if the chamfered surface formed on the one end face of the glass substrate and having a width smaller than that of the chamfered surface of the opposite end face may be formed on each of opposite sides of the one end face adjacent to opposite principal surfaces of the glass substrate, respectively. In this case, in a region of the glass substrate from the depth corresponding to the width of the chamfered surface of the one end face to the depth corresponding to the width of the chamfered surface of the opposite end face, the light introduced from the one end face and a light thus introduced and then totally reflected by the chamfered surface of the opposite end face propagate. Therefore, it is possible to improve a sensitivity of detection of the internal defects in the above-mentioned region.

According to an aspect of the invention, the internal defects of the synthetic silica glass substrate are detected in the production process of the glass substrate for a mask blank at an early stage before precision polishing of the principal surfaces. Therefore, the principal surfaces are precision-polished only for those synthetic silica glass substrates free from the internal defects without executing an unnecessary work of precision-polishing the principal surfaces for the synthetic silica glass substrates having the internal defects.

According to an aspect of the invention, the mask blank is produced by the use of the glass substrate for a mask blank, an exposure mask being produced by patterning a thin film of the mask blank, and a semiconductor device being produced by the use of the exposure mask. Therefore, when pattern transfer is carried out using the exposure mask to transfer the mask pattern of the exposure mask to an object, the exposure mask does not have a region where optical characteristics locally changes (for example, transmittance is decreased) due to the internal defects because the exposure mask uses the synthetic silica glass substrate having no internal defect in a substantially entire region including the vicinity of the principal surface on which the mask pattern is to be formed. Therefore, it is possible to improve the transfer accuracy without giving an adverse influence upon pattern transfer to cause transfer pattern defects.

DESCRIPTION OF THE PREFERRED EMBODIMENTS

Figure 1A:
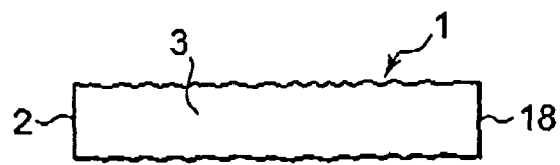
FIGS. 1A to 1H are views for describing methods of producing a glass substrate for a mask blank, a mask blank, and an exposure mask according to one embodiment of this invention.
Figure 1B:
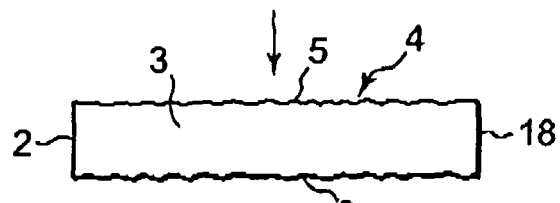

Now, description will be made of a preferred embodiment of this invention with reference to the drawing. In the following description, an ArF excimer laser light (having an exposure wavelength of 193 nm) having an exposure wavelength of 200 nm or less is used as an exposure light.

(A) Method of Producing a Glass Substrate for a Mask Blank

Referring to FIG. 1, a synthetic silica glass ingot is prepared according to the production process disclosed in Japanese Unexamined Patent Application Publications (JP-A) Nos. H8-31723 or 2003-81654. By cutting the synthetic silica glass ingot, a synthetic silica glass plate 1 having a dimension of about 152.4 mm×about 152.4 mm×about 6.85 mm is obtained (FIG. 1A). The synthetic silica glass plate 1 has principal surfaces 5 and 6 opposite to each other. The synthetic silica glass plate 1 is subjected to chamfering. The synthetic silica glass plate 1 also has an end face 2 through which a short-wavelength light having a wavelength of 200 nm or less (in this embodiment, an exposure-wavelength light (an ArF excimer laser light)) as an inspection light is introduced. The synthetic silica glass plate 1 further has an end face 3 adjacent to the end face 2 and receiving lights 15 and 17 generated by internal defects 16 (FIG. 2) and by a remaining region of the synthetic silica glass plate 1 except the internal defects 16. The synthetic silica glass plate 1 still further has an end face 18 adjacent to the end face 3 and opposite to the end face 2 and an end face 19 adjacent to the end face 18 and opposite to the end face 3. The end face 2 is perpendicular to the principal surfaces 5 and 6. Typically, the end faces 3, 18, and 19 are perpendicular to the principal surfaces 5 and 6. Among these surfaces of the synthetic silica glass plate 1, at least the end faces 2 and 3 are mirror-polished to a level sufficient to introduce the exposure-wavelength light. Thus, a synthetic silica glass substrate 4 is prepared (FIG. 1B).

In the above-mentioned preparation step, among the surfaces of the synthetic silica glass substrate 4, the remaining end faces 18 and 19 and the principal surfaces 5 and 6 opposite to each other are not mirror-polished and have a surface roughness of about 0.5 μm. On the other hand, the end faces 2 and 3 have a surface roughness of about 0.03 μm or less. The shapes of the end faces 2, 3, 18, and 19 of the synthetic silica glass substrate 4 prepared in the preparation step will later be described in detail.

Figure 2:
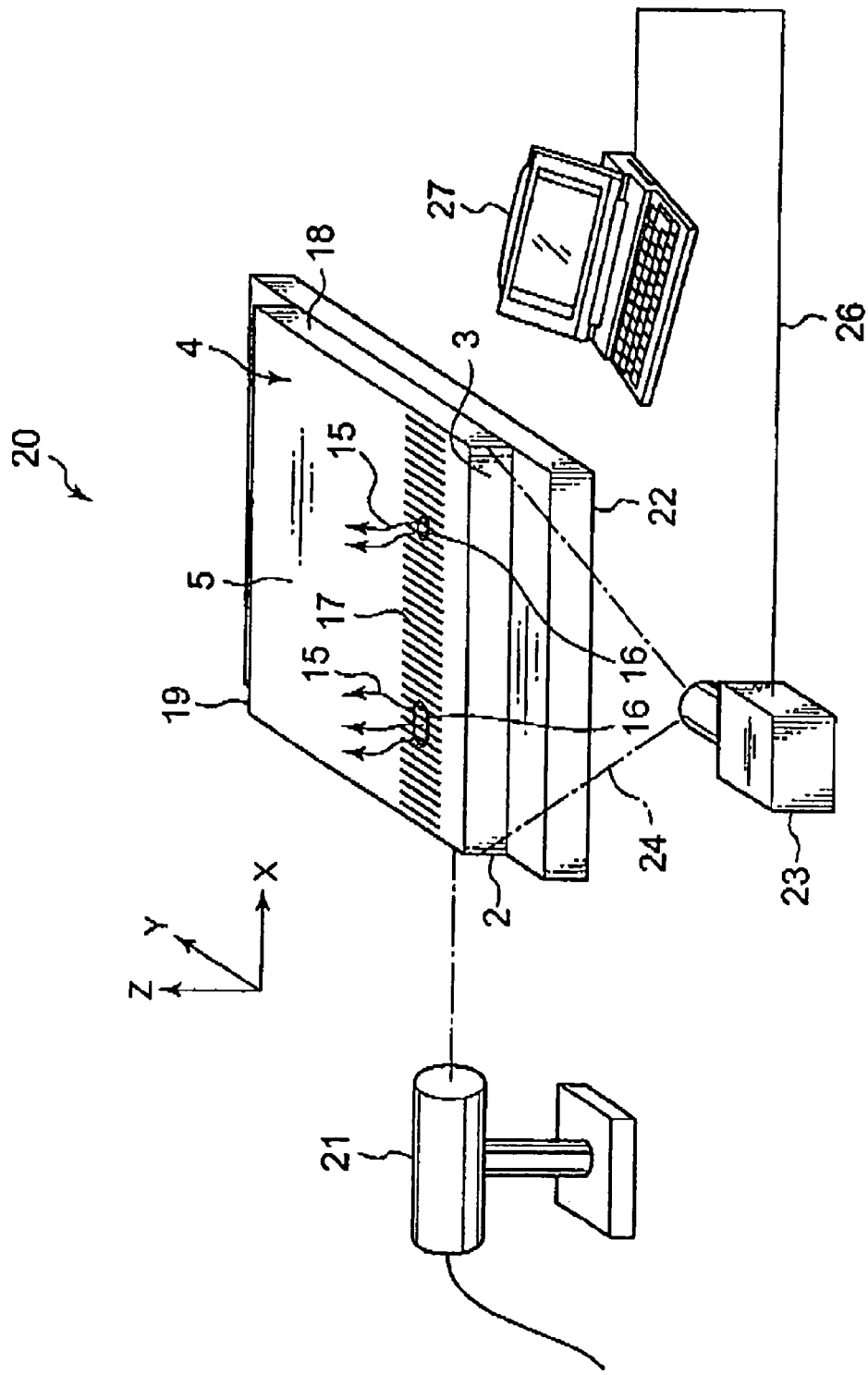
FIG. 2 is a perspective view of a defect inspection apparatus used in a defect inspection method according to one embodiment of this invention.

Next, the synthetic silica glass substrate 4 is mounted to a defect inspection apparatus 20 illustrated in FIG. 2. The ArF excimer laser light is introduced through the one end face 2 of the synthetic silica glass substrate 4. A long-wavelength light (fluorescence) 15 generated by the internal defects 16 present in the synthetic silica glass substrate 4 and having a wavelength longer than that of the exposure-wavelength light is received from the end face 3 of the synthetic silica glass substrate 4 adjacent to the end face 2, together with a long-wavelength light (fluorescence) 17 generated by the remaining region of the synthetic silica glass substrate 4 except the internal defects 16 and having a wavelength longer than the exposure wavelength. With reference to a difference in light amount between the light 15 and the light 17 thus received, a detection step of detecting the internal defects 16 is executed.

Among the internal defects 16 present in the synthetic silica glass substrate 4, some of the internal defects 16 do not cause a problem if an exposure light source has a wavelength longer than 200 nm (for example, a KrF excimer laser (having a wavelength of 248 nm)) but is problematic if the exposure light source has a wavelength of 200 nm or less, for example, an ArF excimer laser. As such internal defects 16, local cords, inclusions, and heterogeneous matters are known. When an exposure mask 14 is produced from the synthetic silica glass substrate 14 through a glass substrate 7 for a mask blank and a mask blank 9 and pattern transfer is carried out by the use of the exposure light having a wavelength of 200 nm or less to transfer a mask pattern of the exposure mask 14 to an object, these internal defects 16 cause local change in optical characteristics (for example, decrease in transmittance) and give an adverse influence upon pattern transfer to decrease a transfer accuracy.

The above-mentioned "local cords" are formed in a region where a very small amount of metal elements are mixed in a synthetic silica glass during synthesis of the synthetic silica glass. If the local cords are present in the glass substrate 7 of the exposure mask 14, the transmittance is decreased by about 20 to 40% upon pattern transfer to decrease the transfer accuracy. The "inclusions" are formed in a region where a greater amount of metal elements are mixed in the synthetic silica glass as compared with the local cords. When the inclusions are present in the glass substrate 7 of the exposure mask 14, the transmittance is decreased by about 40 to 60% during pattern transfer. Further, the "heterogeneous matters" are formed in an oxygen-excessive region where an excessive amount of oxygen is mixed in the synthetic silica glass. After irradiation of a high-energy light, this defect is not remedied. When the heterogeneous matters are present in the glass substrate 7 of the exposure mask 14, the transmittance is decreased by about 5 to 15% during pattern transfer.

The defect inspection apparatus 20 executes the above-mentioned detection step to detect the internal defects 16 (local cords, inclusions, heterogeneous matters, and so on causing local change in optical characteristics during pattern transfer). As illustrated in FIG. 2, the defect inspection apparatus 20 comprises a laser irradiation unit 21 as light introducing means, an XYZ stage 22, a CCD camera (line sensor camera) 23 as light receiving means, and a computer 27 as detecting means.

The laser irradiation unit 21 introduces the ArF excimer laser light (ArF excimer laser beam) as the exposure-wavelength light (i.e., a light having a wavelength same as the exposure wavelength) as the short-wavelength light into the end face 2 of the synthetic silica glass substrate 4. The XYZ stage 22 is adapted to mount the synthetic silica glass substrate 4 to move the synthetic silica glass substrate 4 in a direction X, a direction Y, and a direction Z with respect to a laser beam emitted by the laser irradiation unit 21. The CCD camera (line sensor camera) 23 is arranged on a side faced to the end face 3 of the synthetic silica glass substrate 4 mounted on the XYZ stage 22 and comprises a CCD element (not shown) and a lens (not shown) for widening a detection range of the CCD element. The CCD camera 23 has a detection field 24 throughout an entire range of the synthetic silica glass substrate 4 in a widthwise direction (i.e., an irradiation direction of the laser beam emitted from the laser irradiation unit 21). The computer 27 is connected to the CCD camera 23 via a USB cable 26.

The laser irradiation unit 21 introduces the ArF excimer laser beam into respective positions of the end face 2 of the synthetic silica glass substrate 4 in the direction Y (i.e., a longitudinal direction of the end face 2) while the XYZ stage 22 moves the synthetic silica glass substrate 4 in the direction Y. In response to the ArF excimer laser beam (having a wavelength $\lambda 1$) incident to the respective positions on the end face 2 of the synthetic silica glass substrate 4 in the direction Y, the synthetic silica glass substrate 4 generates the long-wavelength lights 15 and 17 having a wavelength longer than the wavelength $\lambda 1$. The CCD camera 23 receives the long-wavelength lights 15 and 17 on the side of the end face 3 of the synthetic silica glass substrate 4 for each of the respective positions of the synthetic silica glass substrate 4 in the direction Y to pick up an image. In this embodiment, the CCD camera 23 is a monochromatic camera and receives contrast or bright-dark conditions of the lights 15 and 17 to pick up an image.

Supplied with the image from the CCD camera 23, the computer 27 carries out image processing for each position of the synthetic silica glass substrate 4 in the direction Y and analyzes, in relation to an X-direction position of the synthetic silica glass substrate 4, the light amounts (intensities) of the lights 15 and 17 received by the CCD camera 23 for each position of the synthetic silica glass substrate 4 in the direction Y. Specifically, when the lights 15 and 17 have local light amounts greater than a predetermined threshold, the computer 27 judges that the lights 15 and 17 having the local light amounts greater than the predetermined threshold are generated by the internal defects 16. Then, the computer 27 identifies and detects positions of the internal defects 16 (X-direction and Y-direction positions of the synthetic silica glass substrate 4) and the types (local cords, inclusions, heterogeneous matters) of the internal defects 16 with reference to the profile of the lights 15 generated by the internal defects 16 and having the local light amounts.

Figure 3A:
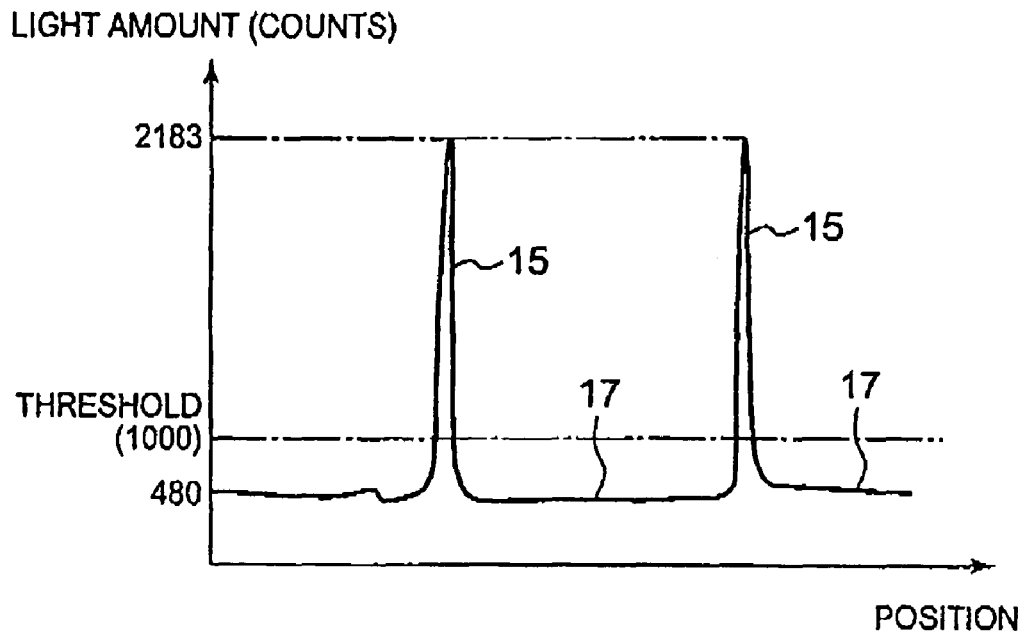
FIGS. 3A and 3B are graphs showing intensity distribution of received lights, obtained by image processing by a computer illustrated in FIG. 2.

For example, it is assumed that the local cords or the inclusions are present in the synthetic silica glass substrate 4 as the internal defects 16. In this case, when the ArF excimer laser beam is introduced from the laser irradiation unit 21 to the synthetic silica glass substrate 4, the local cords or the inclusions generate the lights 15 of the local light amounts greater than the predetermined threshold (1000 counts) as shown in FIG. 3A. The remaining region of the synthetic silica glass substrate 4 except the local cords or the inclusions generates the lights 17. The computer 27 carries out image processing and analysis for the lights 15 and 17 received by the CCD camera 23 to judge the internal defects 16 as the local cords or the inclusions with reference to the profile of the lights 15 of the local light amount greater than the predetermined threshold. Further, assuming that the local cords or the inclusions are present at positions at which the lights 15 of the local light amount greater than the predetermined threshold are generated, the computer 27 detects the local cords or the inclusions together with their positions. In FIG. 3A, the abscissa represents the X-direction positions of the synthetic silica glass substrate 4 and the ordinate represents the light amounts (intensities) of the lights 15 and 17.

Figure 3B:
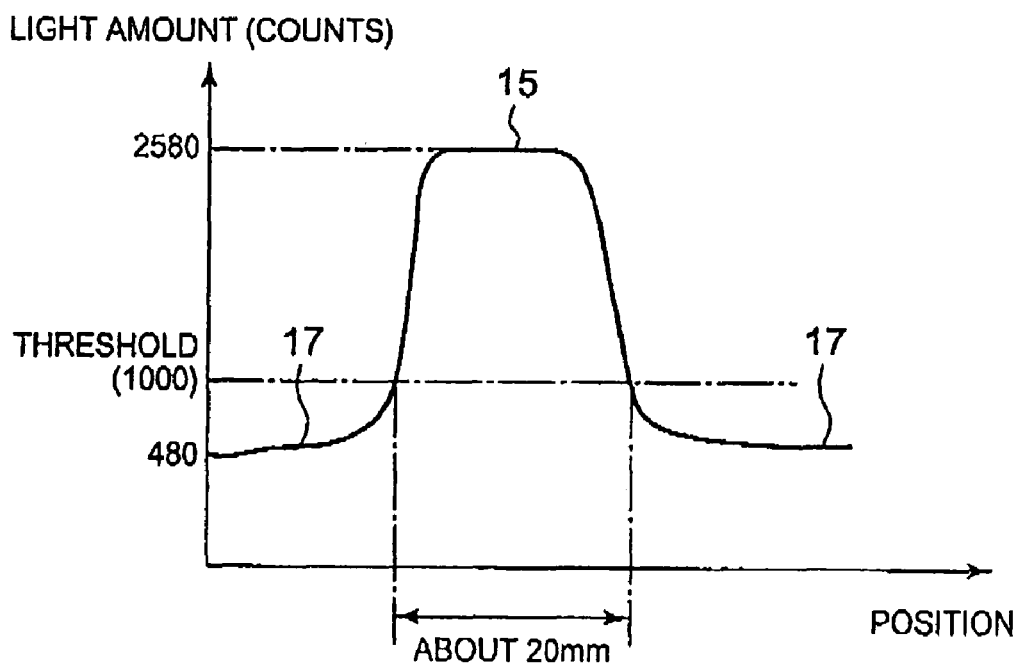

Next, it is assumed that the heterogeneous matters are present in the synthetic silica glass substrate 4 as the internal defects 16. In this case, when the ArF excimer laser beam is introduced from the laser irradiation unit 21 to the synthetic silica glass substrate 4, the heterogeneous matters generate the lights 15 of the local light amounts greater than the predetermined threshold (1000 counts) in a predetermined range (for example, 20 to 50 mm) as shown in FIG. 3B. The remaining region of the synthetic silica glass substrate 4 except the heterogeneous matters generates the lights 17. The computer 27 carries out image processing and analysis for the lights 15 and 17 received by the CCD camera 23 to judge the internal defects 16 as the heterogeneous matters with reference to the profile of the lights 15 of the local light amount greater than the predetermined threshold. Further, assuming that the heterogeneous matters are present at positions at which the lights 15 of the local light amount greater than the predetermined threshold are generated, the computer 27 detects the heterogeneous matters together with their positions. In FIG. 3B also, the abscissa represents the X-direction positions of the synthetic silica glass substrate 4 and the ordinate represents the light amounts (intensities) of the lights 15 and 17.

Figure 1C:
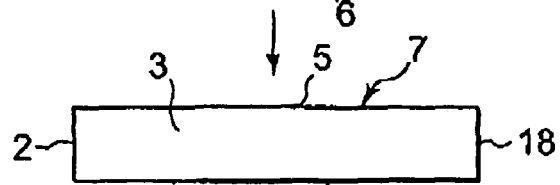

If the internal defects 16 are not detected by the defect inspection apparatus 20, the principal surfaces 5 and 6 of the synthetic silica glass substrate 4 are subjected to mirror polishing and precision polishing so that the principal surfaces 5 and 6 have a desired surface roughness. Then, the synthetic silica glass substrate 4 is subjected to cleaning. Thus, the glass substrate 7 for a mask blank is obtained (FIG. 1C). Preferably, the surface roughness of the principal surfaces 5 and 6 is equal to 0.2 nm or less in root-mean-square roughness (RMS).

Figure 4:
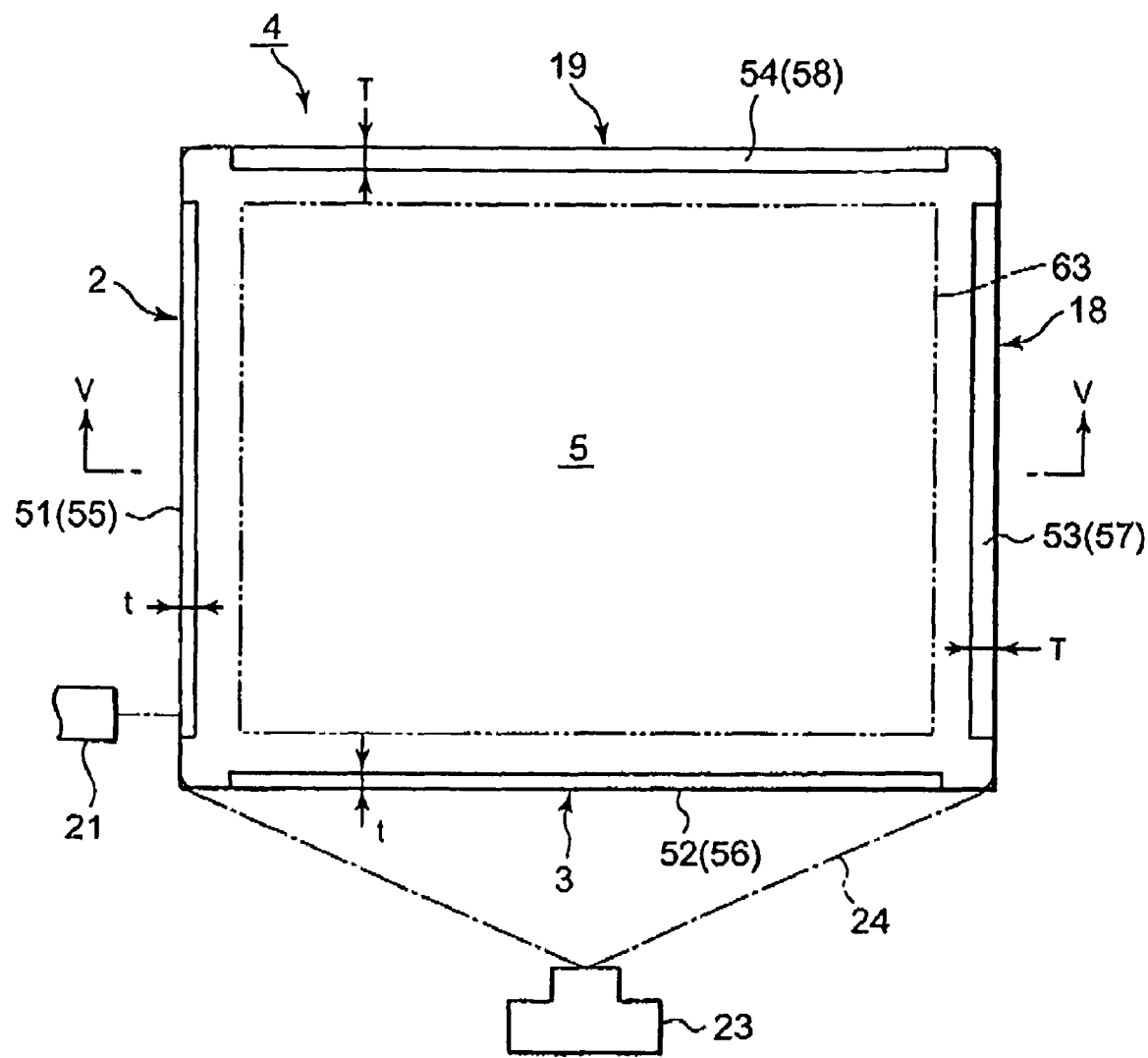
FIG. 4 is a plan view showing a synthetic silica glass substrate illustrated in FIG. 2.
Figure 5A:
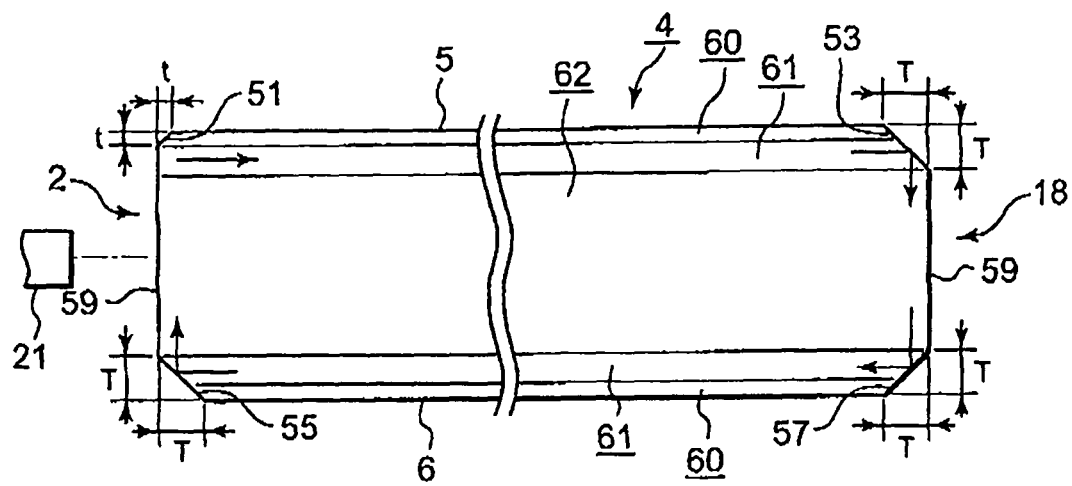
FIG. 5A is a sectional view taken along a line V-V in FIG. 4.
Figure 5B:
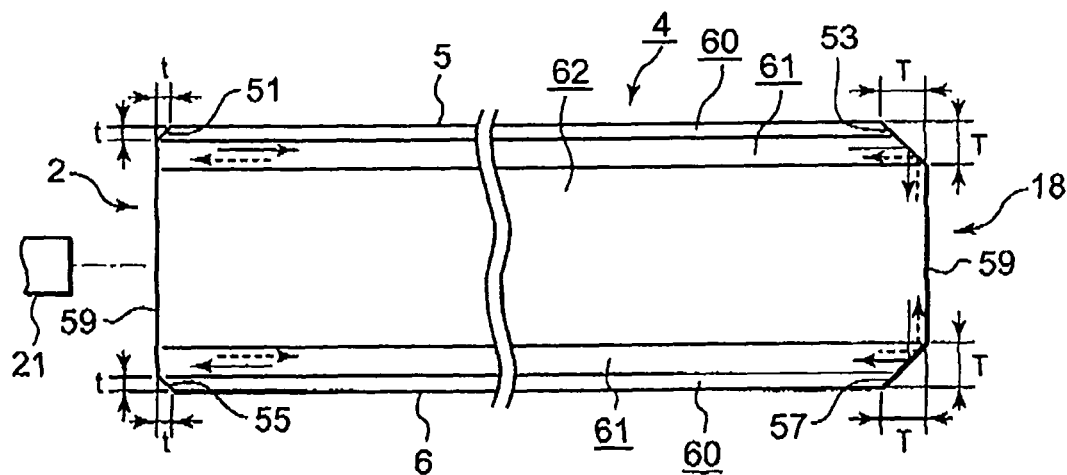
FIG. 5B is a sectional view similar to FIG. 5A and showing a modification of the glass substrate.

In the meanwhile, the synthetic silica glass substrate 4 to be subjected to detection of the internal defects 16 by the defect inspection apparatus 20 in the detection step as described above is prepared in the preparation step in which chamfered surfaces of the end faces 2 and 3 are adjusted in shape as illustrated in FIGS. 4, 5A, and 5B. Specifically, each end face of the synthetic silica glass substrate 4 generally has a side surface perpendicular to the principal surfaces 5 and 6, and chamfered surfaces formed at positions adjacent to the side surface and the principal surfaces 5 and 6. Among those, each of the chamfered surfaces 51 and 52 formed on one sides of the end faces 2 and 3 (i.e., on the sides adjacent to the principal surface 5) has a width t smaller than a width T of the chamfered surface 53 formed on one side of the end face 18 faced to the end face 2 (i.e., on the side adjacent to the principal surface 5). In case where the synthetic silica glass substrate 4 has a dimension of 152.4 mm×152.4 mm×6.85 mm, the width t of each of the chamfered surface 51 of the end face 2 and the chamfered surface 52 of the end face 3 is equal to about 0.2 mm while the width T of the chamfered surface 53 of the end face 18 is equal to about 0.6 mm.

The width of each of the chamfered surfaces 55, 56, and 57 formed on the other sides of the end faces 2, 3, and 18 and adjacent to the principal surface 6 is substantially equal to the width T of the chamfered surface 53 of the end face 18. Similarly, the width of each of the chamfered surfaces 54 and 58 which are formed on opposite sides of the end face 19 faced to the end face 3 and which are adjacent to the principal surfaces 5 and 6 is substantially equal to the width T of the chamfered surface 53 of the end face 18. Four lateral edges at which the end faces 2, 3, 18, and 19 are adjacent to one another are subjected to chamfering to have a curved surface.

Herein, an internal region of the synthetic silica glass substrate 4 is divided into a surface layer region 60, an intermediate region 61, and a main region 62. The surface layer region 60 is a region from each of the principal surfaces 5 and 6 to the depth corresponding to the width t of each of the chamfered surfaces 51 and 52 (i.e., a region from each of the principal surfaces 5 and 6 to the depth of about 0.2 mm). The intermediate region 61 is a region from the depth corresponding to the width t of each of the chamfered surfaces 51 and 52 to the depth corresponding to the width T of each of the chamfered surfaces 53 and 58 (i.e., a region from the depth of about 0.2 mm to the depth of about 0.6 mm). The main region 62 is a region deeper than the depth corresponding to the width T of each of the chamfered surfaces 53 to 58, i.e., a remaining region of the internal region of the synthetic silica glass substrate 4 except the surface layer region 60 and the intermediate region 61.

It is sufficient that each of the chamfered surfaces 51 to 58 is formed in an area corresponding to a pattern forming region 63 where a mask pattern is to be formed when the exposure mask 14 is produced from the synthetic silica glass substrate 4 shown in FIG. 4. Alternatively, the chamfered surfaces 51 through 58 may be formed throughout entire lengths of the end faces 2, 3, 18, and 19.

In the detection step, the ArF excimer laser beam having a beam profile of 7.0 mm×4.0 mm, a power of 6 mJ, and a frequency of 50 Hz is emitted from the laser irradiation apparatus 21 and introduced to the mirror-polished end face 2 as shown in FIG. 5A. An introducing direction is perpendicular to the side surface 59 of the end face 2. Therefore, the ArF excimer laser beam is refracted at the chamfered surface 51, propagates through the synthetic silica glass substrate 4, and leaks out without reaching the end face 18. Therefore, the ArF excimer laser beam does not propagate in the surface layer region 60 so that the internal defects 16 present in the surface layer region 60 can not be detected.

On the other hand, in the intermediate region 61, the ArF excimer laser beam travels straight from the end face 2 towards the end face 18 opposite thereto, is totally reflected by the chamfered surfaces 53 and 57 of the end face 18, and advances towards the chamfered surface 55 of the end face 2. Therefore, it is possible to detect the internal defects 16 present in the intermediate region 61 by the ArF excimer laser beam propagating through the intermediate region 61. In the main region 62 also, the ArF excimer laser beam travels straight from the side surface 59 of the end face 2 towards the side surface 59 of the end face 18. Therefore, it is possible to detect the internal defects 16 present in the main region 62 by the ArF excimer laser beam propagating through the main region 62.

Thus, in the synthetic silica glass substrate 4, in the intermediate region 61 and the main region 62 except the surface layer region 60, the lights 15 and 17 (FIG. 2) are generated by the internal defects 16 present in the intermediate region 61 and the main region 62 and by the remaining region except the internal defects 16. The lights 15 and 17 are received by the CCD camera 23 and analyzed by the computer 27 so as to detect the internal defects 16 present in the intermediate region 61 and the main region 62. The surface layer region 60 is eventually removed in mirror polishing and precision polishing steps of polishing the principal surfaces 5 and 6 after the detection step. Therefore, even if the internal defects 16 are present in the surface layer region 60, the internal defects 16 are eventually removed so that no problem arises. Thus, in the detection step using the defect inspection apparatus 20, it is possible to successfully detect the internal defects 16 in a substantially entire region of the synthetic silica glass substrate 4, including those internal defects 16 in the vicinity of the principal surfaces 5 and 6. After removing the surface layer region 60 from the synthetic silica glass substrate 4 for which the internal defects 16 are not detected in the detection step, the glass substrate 7 for a mask blank is produced from the synthetic silica glass substrate 4. The glass substrate 7 has no internal defect 16 in all regions including the vicinity of the principal surfaces 5 and 6.

In view of the above, in the synthetic silica glass substrate 4, the width t of each of the chamfered surface 51 of the end face 2 and the chamfered surface 52 of the end face 3 is determined in correspondence to a polishing amount of the principal surface 5 adjacent to the chamfered surfaces 51 and 52. Thus, the width t of each of the chamfered surfaces 51 and 52 is appropriately determined according to operations to be executed after the detection step. For example, if the detection step is executed after a final polishing step, the width t of each of the chamfered surfaces 51 and 52 is determined to be extremely small, preferably, to be equal to 0, because of no polishing amount after the detection step.

(B) Method of Producing a Mask Blank

Figure 1D:
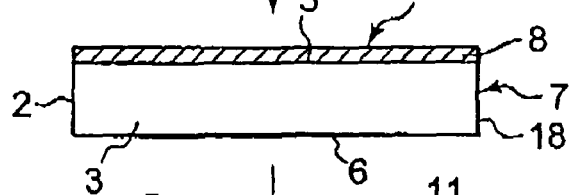

Next, on the principal surface 5 of the glass substrate 7 for a mask blank, a thin film (halftone film) 8 to become a mask pattern is formed by sputtering. Thus, the mask blank (halftone phase shift mask blank) 9 is produced (FIG. 1D). The halftone film 8 is deposited by the use of a sputtering apparatus having a structure which will presently be described.

Figure 6:
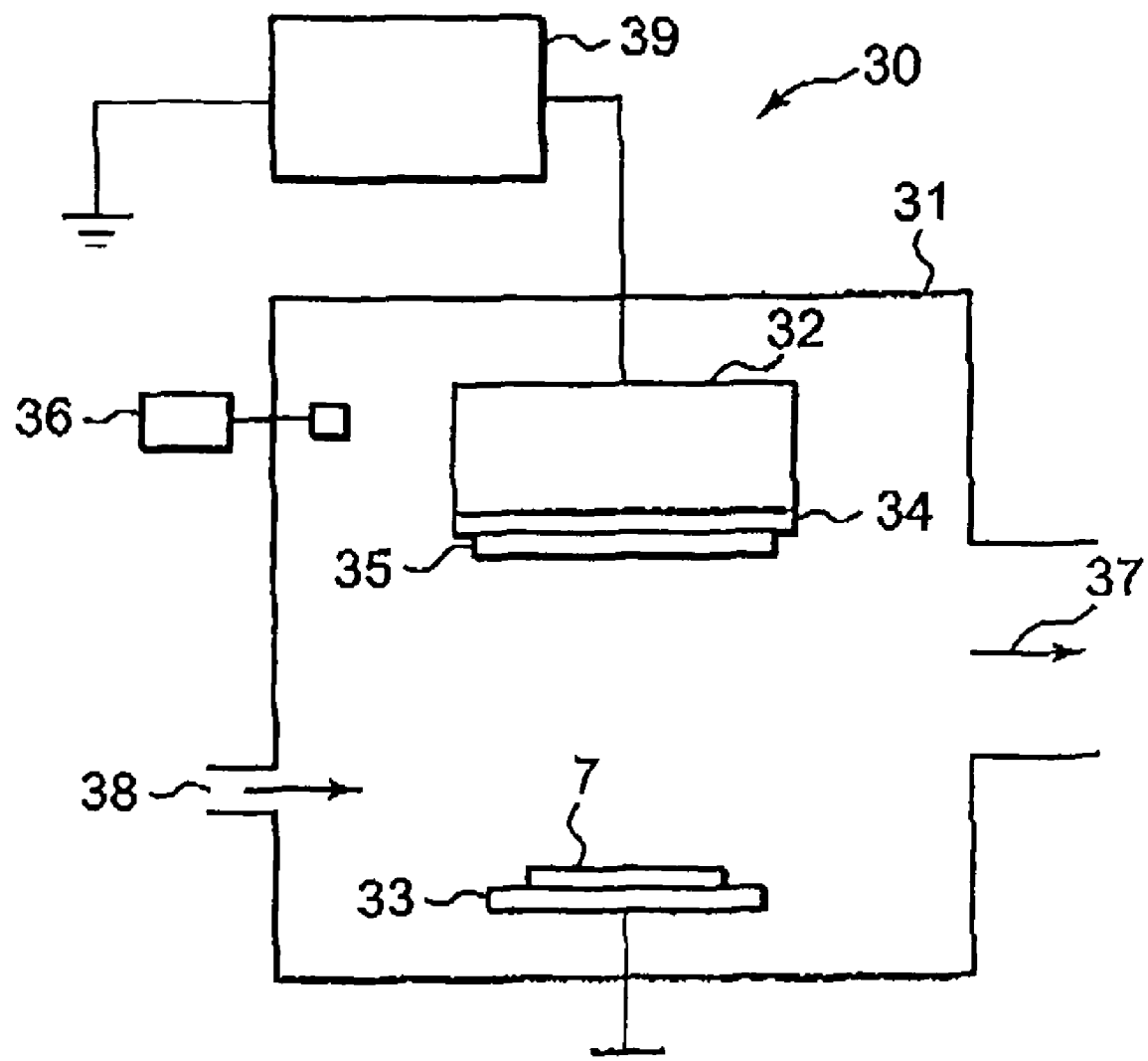
FIG. 6 is a schematic side view showing a sputtering apparatus used in a production process of the mask blank illustrated in FIG. 1.

The sputtering apparatus is a DC magnetron sputtering apparatus 30 as illustrated in FIG. 6. The DC magnetron sputtering apparatus 30 comprises a vacuum chamber 31 in which a magnetron cathode 32 and a substrate holder 33 are disposed. To the magnetron cathode 32, a sputtering target 35 adhered to a backing plate 34 is mounted. For example, oxygen-free steel is used as the backing plate 34 and indium is used to adhere the sputtering target 35 and the backing plate 34. The backing plate 34 is directly or indirectly cooled by a water cooling mechanism. The magnetron cathode 32, the backing plate 34, and the sputtering target 35 are electrically coupled to one another. The glass substrate 7 is mounted to the substrate holder 33.

The vacuum chamber 31 in FIG. 6 is evacuated by a vacuum pump (not shown) via an exhaust port 37. After an atmosphere in the vacuum chamber 31 reaches a degree of vacuum which does not affect characteristics of a film to be formed, a mixed gas containing nitrogen is introduced via a gas inlet port 38. By the use of a DC power supply 39, the magnetron cathode 32 is applied with a negative voltage to carry out sputtering. The DC power supply 39 has an arc detecting function and monitors a discharging condition during sputtering. A pressure gauge 36 measures an internal pressure of the vacuum chamber 31.

(C) Method of Producing an Exposure Mask

Figure 1E:
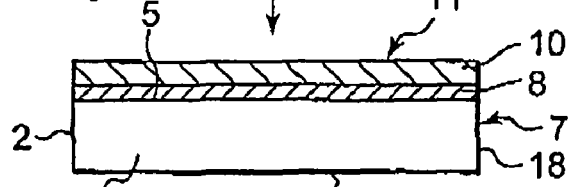

Next, a resist is applied to a surface of the halftone film 8 of the mask blank (halftone phase shift mask blank) 9 and then heated to form a resist film 10 (FIG. 1E).

Figure 1F:
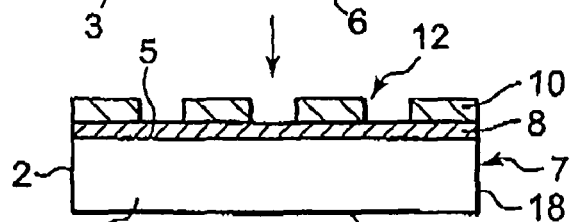

Next, a predetermined pattern is written on the resist film 10 of a resist-coated mask blank 11 and developed to form a resist pattern 12 (FIG. 1F).

Figure 1G:
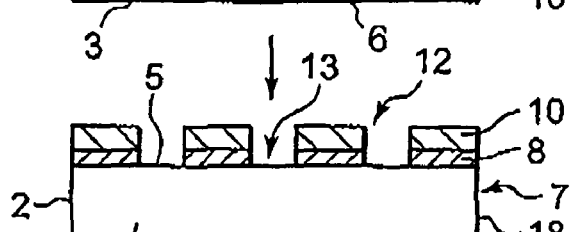
Figure 1H:
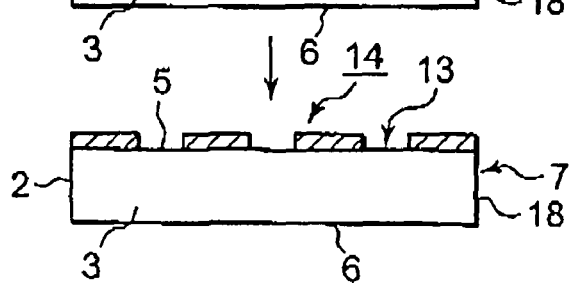

Then, with the resist pattern 12 used as a mask, the halftone film 8 is etched by dry etching to form a halftone film pattern 13 as a mask pattern (FIG. 1G).

Finally, the resist pattern 12 is removed to obtain the exposure mask 14 with the halftone film pattern 13 formed on the glass substrate 7.

(D) Method of Producing a Semiconductor Device

The exposure mask 14 thus obtained is mounted to an exposure apparatus. By the use of the photolithography using the exposure mask 14 and the ArF excimer laser as the exposure light, the mask pattern of the exposure mask 14 is transferred to a resist film formed on a semiconductor substrate (semiconductor wafer) to form a desired circuit pattern on the semiconductor substrate. Thus, a semiconductor device is produced.

(E) Effect of the Embodiment

With the above-mentioned structure, the foregoing embodiment exhibits the following effects (1) through (3)

(1) The exposure-wavelength light (ArF excimer laser beam) as the short-wavelength light having a wavelength of 200 nm or less is introduced to the synthetic silica glass substrate 4 to be used for inspection of the internal defects 16 in the glass substrate 4. Thus, it is possible to successfully detect the internal defects 16 which become transfer pattern defects when pattern transfer is carried out by the use of the exposure light and the exposure mask 14 produced from the synthetic silica glass substrate 4 through the glass substrate 7 for a mask blank and the mask blank 9. By the use of the synthetic glass substrate 4 for which the internal defects 16 are not detected, the glass substrate 7 for a mask blank is produced. The exposure mask 14 using the glass substrate 7 does not have a region in which the optical characteristics are locally changed (for example, the transmittance is decreased) due to the internal defects 16. Therefore, it is possible to improve the transfer accuracy without causing the transfer pattern defects.

(2) In the preparation step, the synthetic silica glass substrate 4 is prepared in which the width t of the chamfered surface 51 of the end face 2 through which the ArF excimer laser beam is introduced is smaller than the width T of the chamfered surface 53 of the end face 18 opposite to the end face 2. Therefore, in the surface layer region 60 of the synthetic silica glass substrate 4 from the principal surface 5 adjacent to the chamfered surface 51 having a smaller width to the depth corresponding to the width t of the chamfered surface 51, the ArF excimer laser beam introduced perpendicularly to the side surface 59 of the end face 2 is refracted at the chamfered surface 51 of the end face 2, propagates through the synthetic silica glass substrate 4, and leaks out without reaching the end face 18. Therefore, the internal defects 16 present in the surface layer region 60 can not be detected. On the other hand, in the intermediate region 61 and the main region 62 except the surface layer region 60, the ArF excimer laser beam introduced to the end face 2 reaches the end face 18. Therefore, the internal defects 16 in these regions 61 and 62 can be detected. It is noted here that the surface layer region 60 is eventually removed in the mirror polishing and the precision polishing steps of polishing the principal surfaces 5 and 6, which will be executed later. Therefore, even if the internal defects 16 are present in the surface layer region 60, the internal defects 16 are eventually removed and no problem occurs.

Therefore, it is possible to successfully detect the internal defects 16 in a substantially entire region of the synthetic silica glass substrate 4, including those internal defects in the vicinity of the principal surface 5 on which the mask pattern (halftone film pattern 13) is to be formed when the exposure mask 14 is produced from the synthetic silica glass substrate 4. In the synthetic silica glass substrate 4, the internal defects 16 in the vicinity of the principal surface 5 on which the mask pattern is to be formed are easily focused and transferred onto the object (for example, a semiconductor wafer) when pattern transfer to the object is carried out by the use of the exposure mask 14, while the internal defects 16 at other positions of the synthetic silica glass substrate 4 are hardly focused on the object in relation to a focal depth of the exposure apparatus. Therefore, the internal defects 16 in the vicinity of the principal surface 5 has a great influence upon pattern transfer. In the detection step, the internal defects 16 particularly in the vicinity of the principal surface 5 are successfully detected. As a result, by producing the exposure mask 14 from the synthetic silica glass substrate 4 for which the internal defects 16 are not detected, it is possible to improve the transfer accuracy of pattern transfer using the exposure mask 14.

(3) In an early stage of the production process of the glass substrate 7 for a mask blank before mirror polishing and precision polishing of the principal surfaces 5 and 6, the internal defects 16 of the synthetic silica glass substrate 4 are detected. Therefore, the principal surfaces 5 and 6 are mirror-polished and precision-polished only for those synthetic silica glass substrates 4 free from the internal defects 16 without executing an unnecessary work of mirror-polishing and precision-polishing the principal surfaces 5 and 6 for the synthetic silica glass substrates 4 having the internal defects 16.

In the foregoing embodiment, in the synthetic silica glass substrate 4 prepared in the preparation step, the width t of each of the chamfered surfaces 51 and 52 of the end faces 2 and 3 on one sides adjacent to the principal surface 5 is smaller than the width T of the chamfered surface 53 of the end face 18. Alternatively, as illustrated in FIG. 5B, both of the chamfered surfaces 51 and 55 of the end face 2 on opposite sides adjacent to the principal surfaces 5 and 6, respectively, and both of the chamfered surfaces 52 and 56 of the end face 3 on opposite sides adjacent to the principal surfaces 5 and 6, respectively, may have the width t smaller than the width T of the chamfered surface 53 of the end face 18. In this case, in the intermediate region 61 of the synthetic silica glass substrate 4, both the light introduced from the side surface 59 of the end face 2 and the light thus introduced and then totally reflected by each of the chamfered surfaces 53 and 57 of the end face 18 propagate. Therefore, the light amount in the intermediate region 61 is increased to improve the sensitivity of detection of the internal defects 16.

Figure 7:
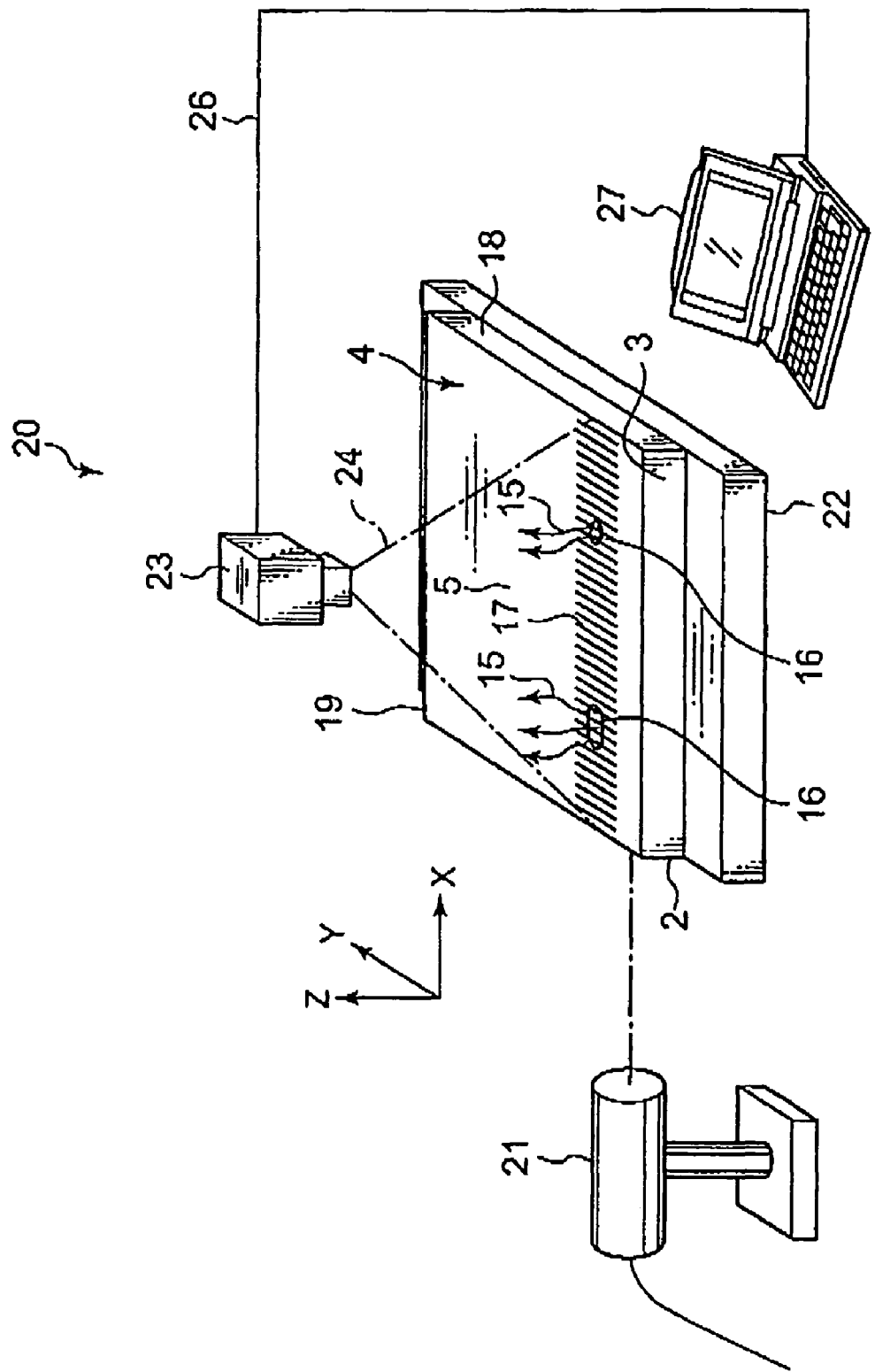
FIG. 7 is a perspective view for describing a defect inspection method according to another embodiment of this invention.

In the foregoing embodiment, the CCD camera 23 for receiving the lights 15 and 17 generated by the internal defects 16 and by the remaining region except the internal defects 16 in the detection step is disposed on the side of the end face 3 adjacent to the end face 2 through which the ArF excimer laser beam is introduced. In another embodiment illustrated in FIG. 7, the CCD camera 23 is disposed on the side of the principal surface 5 or 6. In this case, the width of each of the chamfered surfaces 52 and 56 formed on the end face 3 may be substantially equal to the width T of the chamfered surface 53 of the end face 18. It is noted here that, in the preparation step, the principal surface 5 or 6 must be mirror-polished to a level equivalent to that of the end face 2 through which the ArF excimer laser beam is introduced. In another embodiment also, the effects similar to the effects (1) to (3) in the foregoing embodiment are exhibited.

Although this invention has been described in conjunction with the preferred embodiment thereof, this invention may be modified in various other manners within the scope of the appended claims. For example, in the foregoing embodiment, the ArF excimer laser is used as the exposure light source. However, any light having a wavelength of 200 nm or less, preferably, a wavelength between 100 nm and 200 nm may be used. For example, an F2 excimer laser may be used. Further, in order to obtain the wavelength same as that of the ArF excimer laser or the F2 excimer laser, a light (beam) from a light source such as a deuterium ($D_2$) lamp is split to obtain a light (beam) having a center wavelength same as that of the ArF excimer laser or the F2 excimer laser.

The CCD camera 23, which is a monochromic camera in the foregoing embodiment may be a color camera. The CCD camera 23 receives the lights 15 and 17 generated by the internal defects 16 of the synthetic silica glass substrate 4 and by the remaining region except the internal defects 16 and having a wavelength of 200 nm or less. The computer 27 carries out image processing for the image picked up by the CCD camera 23 for each of red, green, blue colors and detects the internal defects 16 from the light intensity (light amount) of the light image-processed for each color. In this case, the computer 27 may detect the internal defects 16 from information, such as a color and a wavelength, of the light image-processed for each color. Further, detection of the internal defects may be carried out at a final stage of the production process of the glass substrate for a mask blank.

In the foregoing embodiment, the CCD camera 23 receives the lights 15 and 17 having the wavelength longer than the exposure-wavelength light and generated by the internal defects 16 of the synthetic silica glass substrate 4 and by the remaining region except the internal defects 16. Alternatively, these lights 15 and 17 may be received by a spectrometer. In this case, spectral characteristics (wavelength and intensity) of the internal defects 16 or intensity (light amount) distributions of the lights 15 and 17 are measured to detect the internal defects 16.

In the foregoing embodiment, description has been made about the halftone phase shift mask blank having the halftone film formed on the glass substrate. Not being limited thereto, this invention is applicable to a halftone phase shift mask blank having a halftone film formed on the synthetic silica glass substrate 7 and a light shielding film (opaque film) formed on the hafltone film, or a photomask blank having a light shielding film (opaque film) formed on the glass substrate 7 for a mask blank. A resist film may be formed on the light shielding film (opaque film) of the halftone phase shift mask blank or the photomask blank.

What is claimed is:

1. A glass substrate for a mask blank, said glass substrate having two principal surfaces, four end surfaces perpendicular to the principal surfaces, and chamfered surfaces formed at positions adjacent to each of the end surfaces and the principal surfaces, each chamfered surface having a width defined as measurement taken from an adjacent principal surface in a direction parallel to an adjacent end surface, wherein:

a first chamfered surface of the chamfered surface formed at the position adjacent to a first end surface of the end surfaces and a first principal surface of the principal surfaces has a width smaller than that of each of the chamfered surfaces formed on an opposite end face of said glass substrate, said opposite end face being opposite to said first end surface, and the width of said first chamfered surface is sized so as to define a surface layer region of said glass substrate, said surface layer region being a region of said glass substrate from said first principal surface to a depth corresponding to a width of said first chamfered surface, an intermediate region of said glass substrate being defined as a region of said glass substrate from a depth corresponding to the width of said first chamfered surface to a depth corresponding to the width of each of the chamfered surfaces formed on said opposite end face, whereby the width of the first chamfered surface being smaller than the width of the chamfered surfaces of the opposite end face permits an inspection light that is applied in an orthogonal direction with respect to said first end surface proximate said intermediate region to be introduced into said first end surface and to propagate through said intermediate region so that said inspection light travels straight from said first end surface towards said opposite end face and is totally reflected by at least a portion of each of the chamfered surfaces formed on said opposite end face, and whereby an internal defect within the intermediate region generates a fluorescence in response to at least a portion of the inspection light.

2. The glass substrate according to claim 1, wherein a second chamfered surface of the chamfered surface formed at the position adjacent to said first end surface and a second principal surface of the principal surfaces has a width equal to that of each of the chamfered surfaces formed on said opposite end face of said glass substrate.

3. The glass substrate according to claim 1, wherein a second chamfered surface of the chamfered surface formed at the position adjacent to said first end surface and a second principal surface of the principal surfaces has a width equal to that of said first chamfered surface.

4. The glass substrate according to claim 1, wherein the width of said first chamfered surface is determined so that a transfer pattern defect due to an internal defect is not caused during pattern transfer in which a mask pattern of an exposure mask using the glass substrate is transferred to an object.

5. The glass substrate according to claim 1, wherein the inspection light for use in detecting the internal defect of said glass substrate is introduced into said first end surface and has a wavelength of 200 nm or less.

6. A mask blank comprising the glass substrate according to claim 1, and a thin film formed on said first principal surface of said glass substrate to become a mask pattern.

7. An exposure mask comprising the glass substrate according to claim 1, and a thin film patterned to form a mask pattern and formed on said first principal surface of said glass substrate.

8. The glass substrate according to claim 1, wherein said intermediate region ranges from 0.2 mm to 0.6 mm in depth from said first principal surface.

* * * * *